US005546929A

United States Patent [19]

Muchin

[11] Patent Number: 5,546,929
[45] Date of Patent: Aug. 20, 1996

[54] NASAL DILATOR

[76] Inventor: Jerome D. Muchin, 320 Constock Ave., Los Angeles, Calif. 90024

[21] Appl. No.: 499,636

[22] Filed: Jul. 7, 1995

[51] Int. Cl.$^6$ .......................... A61M 15/00; A61M 16/00; A61F 5/08; A62B 7/00
[52] U.S. Cl. .............................. 128/200.24; 128/207.18; 606/199; 606/204.45
[58] Field of Search ......................... 128/200.24, 204.12, 128/206.18, 207.18, 912, DIG. 26; 606/191, 196, 199, 204.45; 602/54, 56, 58

[56] References Cited

U.S. PATENT DOCUMENTS

| | | |
|---|---|---|
| D. 310,565 | 9/1990 | Petruson . |
| 701,538 | 6/1902 | Carence . |
| 850,978 | 4/1907 | Soares . |
| 1,043,924 | 11/1912 | Gottlieb . |
| 1,134,993 | 4/1915 | Bye . |
| 1,256,188 | 2/1918 | Wilson . |
| 1,292,083 | 1/1919 | Sawyer . |
| 1,322,375 | 11/1919 | Un . |
| 1,950,839 | 3/1934 | Chirila . |
| 1,950,926 | 3/1934 | Lobl . |
| 2,001,862 | 5/1935 | Battey . |
| 2,055,855 | 9/1936 | Weaver . |
| 2,221,758 | 11/1940 | Elmquist ................................ 128/154 |

(List continued on next page.)

FOREIGN PATENT DOCUMENTS

| | | |
|---|---|---|
| 2504 | 11/1910 | United Kingdom . |
| 18254 | 11/1911 | United Kingdom . |
| 1435853 | 5/1976 | United Kingdom . |
| WO92/22340 | 12/1992 | WIPO ............................. 128/200.24 |
| WO94/23675 | 4/1994 | WIPO . |

OTHER PUBLICATIONS

Petruson, Bjorn, "Snoring Can Be Reduced When the Nasal Airflow is Increased by the Nasal Dilator Nozovent", *Arch. Otolaryngol Head Neck Surg.* (1990) vol. 116, pp. 462–464.

Petruson, Bjorn; "Improvement of the Nasal Airflow by the Nasal Dilator Nozovent", *Rhinology*, vol. 26, pp. 289–292 (1988).

Petruson, Bjorn; Letter to the Editor, "Better Sleep with Dilated Nose", *Rhinology*, pp. 27, 211–213, (1989).

Petruson, Bjorn; "Decreased Nasal Resistance by the Nasal Dilator Nozovent® can Reduce Snoring", World Congress on Chronic Rhonchopathy, pp. see entire document, (May 1989).

Petruson, Bjorn et al.; "The Importance of Nose–breathing for the Systolic Blood Pressure Rise During Exercise", *Acta Otolaryngol*, Stockholm, 109: 461–466, (1990).

E. N. T. Spring Symposium; "Report of a Symposium at the Royal Society of Medicine, London, May 21, 1991"pp. 1–4, A Simple, but Effective Way to Treat Snoring, Petruson.

Petruson, Bjorn; "Two New Ways for Nasal Administration of Drugs with the Nasal Dilator Nozovent", Abstract, ENT–Department, University of Goteborg, University of Goteborg, Sahlgrens's Hospital, 413, 45 Goteborg, Sweden.

Hoijer, Ulf, et al., "The Effects of Nasal Dilation on Snoring and Obstructive Sleep Apnea", *Arch. Otolaryngol Head Neck Surg. (1992)* vol. 118, pp. 281–284.

Lancer, J. M., et al., "The Francis Alae Nasi Prop and Nasal Airway Resistance to Airflow," *The Journal of Laryngology and Otology* (1986) vol. 100, pp. 539–541.

Ford, Charles, et al., "A Nasal Prothesis for Treatment of Nasal Airway Obstruction," *Rhinology* (1985) vol. 23, pp. 223–229.

*Primary Examiner*—Kimberly L. Asher
*Attorney, Agent, or Firm*—Merchant, Gould, Smith, Edell, Welter & Schmidt

[57] ABSTRACT

A nasal dilator for preventing outer wall tissue of nasal passages of a nose from drawing in during breathing. There is a spring member for bridging a human nose, the spring member extending over the bridge and at least partly beyond the bridge on both sides of the bridge. A pad with an adhesive surface covers the spring member and extends around the spring member so that there is a perimeter of space formed between the spring member and the pad member. The spring is inset centrally in the pad. An adhesive between the spring member and the pad wholly connects the spring member on its entire engaging surface with the pad.

44 Claims, 2 Drawing Sheets

U.S. PATENT DOCUMENTS

| | | |
|---|---|---|
| 2,243,360 | 5/1941 | Slatis et al. . |
| 2,264,153 | 2/1940 | Rowe . |
| 2,273,873 | 2/1942 | Klein ............ 128/156 |
| 2,274,997 | 3/1942 | Thurman . |
| 2,277,390 | 3/1941 | Crespo . |
| 2,398,073 | 4/1946 | Bonde . |
| 2,426,161 | 8/1947 | Biederman . |
| 2,509,157 | 5/1950 | Lind . |
| 2,566,148 | 8/1951 | Sky . |
| 2,586,219 | 2/1952 | Geffas . |
| 2,625,931 | 1/1953 | Phillips . |
| 2,674,245 | 10/1950 | Tanditter . |
| 2,715,904 | 4/1954 | Hill . |
| 2,949,443 | 8/1960 | Merriam et al. ............ 260/80.5 |
| 3,027,897 | 7/1959 | Carofiglio . |
| 3,046,989 | 7/1962 | Hill . |
| 3,426,751 | 2/1969 | Radewan ............ 606/204.45 |
| 3,742,943 | 7/1973 | Malmim . |
| 3,835,848 | 9/1974 | Berner . |
| 3,905,335 | 9/1975 | Kapp . |
| 3,935,859 | 2/1976 | Doyle . |
| 4,153,051 | 5/1979 | Shippert . |
| 4,181,127 | 1/1980 | Linsky et al. ............ 128/155 |
| 4,201,217 | 5/1980 | Slater . |
| 4,213,452 | 7/1980 | Shippert . |
| 4,220,150 | 9/1980 | King . |
| 4,221,217 | 9/1980 | Amezcua . |
| 4,267,831 | 5/1981 | Aguilar M. . |
| 4,274,402 | 6/1981 | Shippert . |
| 4,324,237 | 4/1982 | Buttaravoli ............ 128/214 R |
| 4,327,719 | 5/1982 | Childers . |
| 4,340,040 | 7/1982 | Straith . |
| 4,341,207 | 7/1982 | Steer et al. ............ 128/155 |
| 4,341,208 | 7/1982 | Gordon ............ 128/156 |
| 4,402,314 | 9/1983 | Goode . |
| 4,414,977 | 11/1983 | Rezakhany . |
| 4,485,809 | 12/1984 | Dellas ............ 128/156 |
| 4,534,342 | 8/1985 | Paxa . |
| 4,592,357 | 6/1986 | Ersek . |
| 4,669,458 | 6/1987 | Abraham et al. ............ 128/133 |
| 4,674,133 | 6/1987 | Oschner ............ 2/206 |
| 4,744,355 | 5/1988 | Faasse, Jr. ............ 128/156 |
| 4,823,789 | 4/1989 | Beisang, III . |
| 4,917,112 | 4/1990 | Kalt . |
| 4,932,943 | 6/1990 | Nowak . |
| 4,971,282 | 11/1990 | Dickinson . |
| 4,984,302 | 1/1991 | Lincoln . |
| 4,995,114 | 2/1991 | Price, Jr. . |
| 5,003,971 | 4/1991 | Buckley . |
| 5,022,389 | 6/1991 | Brennan . |
| 5,101,837 | 4/1992 | Perrin . |
| 5,116,675 | 5/1992 | Nash-Morgan . |
| 5,209,801 | 5/1993 | Smith . |
| 5,284,469 | 2/1994 | Jasen et al. . |
| 5,383,891 | 1/1995 | Walker . |
| 5,466,456 | 11/1995 | Glover ............ 424/401 |
| 5,476,091 | 12/1995 | Johnson ............ 128/200.24 |

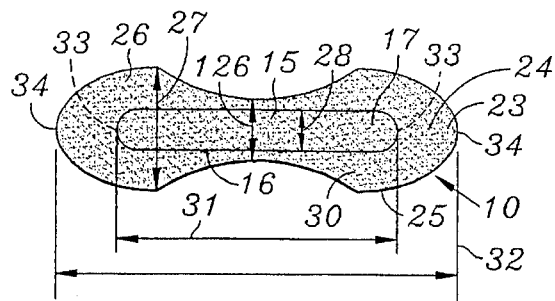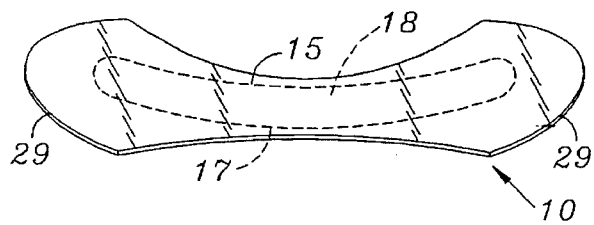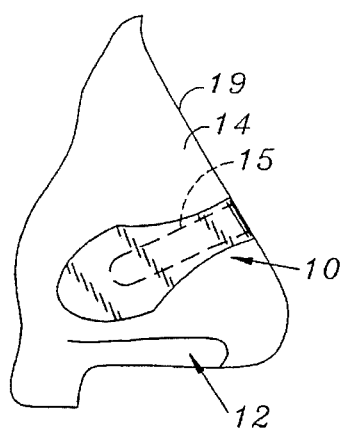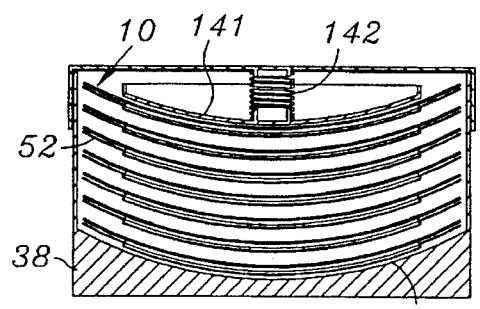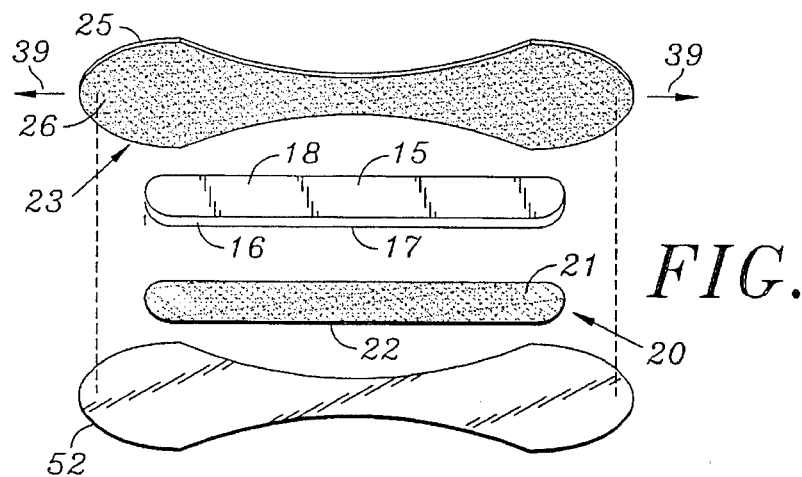

NASAL DILATOR

BACKGROUND

This invention relates to dilators for the nose. In particular, the invention is concerned with a dilator to urge the nasal passages of the nose open during breathing.

One known form of dilator used for this purpose is in the nature of a band for extension over the nose from one nasal passage, over the bridge of the nose, to the other nasal passage. This pad is formed of a flexible material which has sandwiched with it a resilient spring material. Both the flexible material and the spring are normally planar. When the pad is placed on the nose, it sticks to the skin of the nose, and the action of the spring causes the nasal passages to be urged open.

In the Applicant's experience, the known dilator is not as effective as it could be. In particular, the nasal passages are not urged open as much or as little as they could usefully and safely be opened. Also, the currently known device consists of multiple components forming the pad in a sandwich relationship with the spring. Therefore, the fabrication of such a dilator arrangement is unduly complicated.

There is a need to provide a pad system for a dilator for location over the nose which minimizes the disadvantages of known systems.

SUMMARY

By this invention there is provided a dilator which has advantages over known dilators.

According to the invention, there is provided a nasal dilator for preventing outer wall tissue of nasal passages of a human nose from drawing in during breathing. The dilator includes an elongated resilient spring member for bridging a human nose, and there is also a flexible pad having a surface area and peripheral edge. The pad, which is made of a breathable material, engages the spring member, which is a polyflex material, and extends around the spring member.

There is an adhesive between the spring member and the pad such that the spring member on one of its entire engaging surface wholly adheres with the pad. A surface perimeter area of the pad is formed between the outer edge of the spring member and the peripheral edge of the pad. The surface perimeter area includes an adhesive for adhering to skin of the nose.

When the spring member is located over the bridge of the nose, the opposite flat surfaces of the spring member extend over the bridge of the nose and at least partly beyond the bridge of the nose. In this manner, the spring extends over the nasal passages on both sides of the bridge.

In some embodiments, when in use on the nose, there are only the spring member, the adhesive pad, and the adhesive between the pad and the spring member. When in position on the nose, a flat surface of the spring member engages directly on the nose. In some other embodiments, there is also an adhesive on the surface area of the spring adjacent to the bridge of the nose, so the spring member adheres to the nose.

When unattached to the nose, the spring member and pad, has a natural position contrary to a curvature formed by location of the spring member over the bridge of the nose and adjacent to the nasal passages. Preferably, the natural position is with a curvature contrary to the shape of the curvature formed from one nasal passage over the bridge to the second nasal passage. The contrary curvature acts to place an increased amount of spring action on the dilator so that the dilation action on the nasal passages is enhanced when in use.

In one form of the invention, the dilator is located in a package before usage on the nose, and the interaction of the package on the dilator develops the contrary curvature. In another form of the invention, the pad is stretched prior to adhering to the spring, and that stretch acts to place the contrary curvature onto the dilator.

The invention is further described with reference to the accompanying drawings.

DRAWINGS

FIG. 1 is an underview of the dilator showing adhesive on the pad and on the spring.

FIG. 2 is a perspective view from the top of the dilator before being placed on the nose.

FIG. 3 is a side view of the dilator on the nose.

FIG. 4 is a view of multiple dilators in a package to effect the curvature contrary to the position of the dilator on the nose.

FIG. 5 is an exploded perspective top view of the components making up the dilator.

DESCRIPTION

Figure 6:
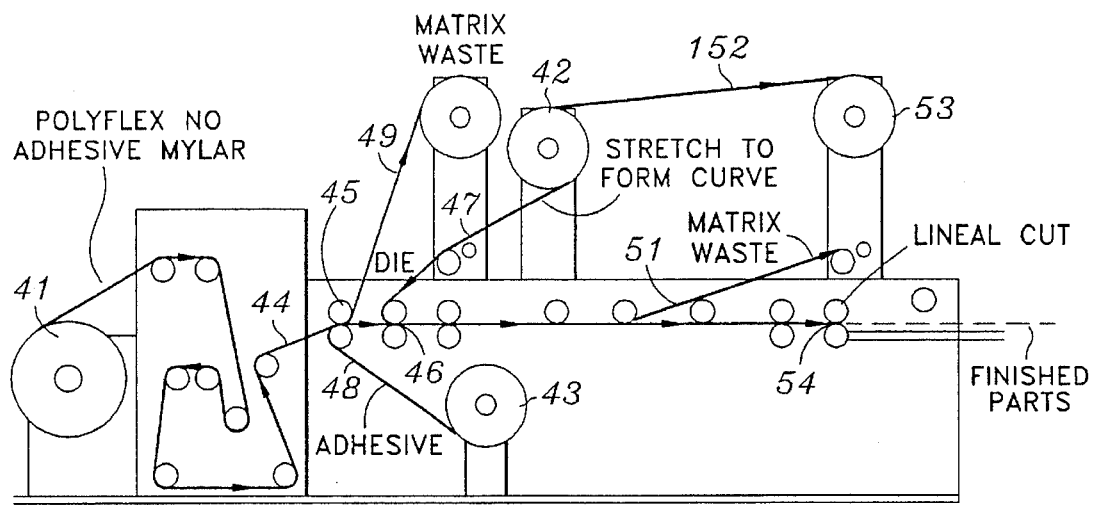
FIG. 6 is a diagrammatic view of a construction procedure for manufacturing the dilator where a stretch is placed on the pad to effect the contrary curvature.

A nasal dilator 10 prevents the outer wall tissue 11 of first and second nasal passages 12 of a human nose 14 from drawing in during breathing.

SPRING

The dilator 10 includes an elongated resilient spring 15 for bridging the human nose 14. The spring member 15 is formed of a synthetic resinous material. The spring member 15 has an outer edge 16 and opposite flat surfaces 17 and 18. The surface 17 extends over a bridge 19 of the nose 14.

The spring material 15 is formed of 0.010" clear polyester film. An acrylic adhesive carrier 20 having a thickness of 0.0015" liner for die cutting is provided on both sides. The adhesive is indicated by numerals 21 and 22.

The film 15 is clear, durable, and has dimensional stability. It is resistant to mild acids, alkalies, and salt. Further, the film 15 is fungus, water and corrosion-resistant.

PAD

The dilator 10 includes a flexible adhesive pad 23 having a surface area 24 and peripheral edge 25. The pad 23 engages the spring member 15 and extending around the spring member 15.

The pad material 23 is preferably 9906T, 3M Elastic Nonwoven Tape from 3M Company, 3M Center, St. Paul, Minn. The product is a tan elastic polyurethane tape coated on one side with an acrylate adhesive 26. The tape is supplied on a paper liner 152 with the liner on the inside of the roll.

The backing of the tape is nonwoven of tan-colored polyurethane fibers. The adhesive is a hypoallergenic, pressure-sensitive acrylate. The liner is a silicone-coated kraft paper.

SPRING AND PAD

The spring member 15 occupies about 25% to about 50% of the surface area 24 of the pad 23. The spring member 15 is centrally located in the surface area 24 of the pad 23.

The peripheral edge 25 of the pad 23 defines a narrow width 26 and a broad width 27. The narrow width 26 is substantially for location over the bridge 19 of the nose 14. The broad width 27 is substantially for location centrally over the nasal passages 12 of the nose 14.

The spring member 15 defines a width 28. The width 28 of the spring member 15 being about one-half to three-quarters of the width of narrow width 26 of the pad 23. The pad 23 is an elongated element with rounded ends 29.

The spring member 15 defines a length 31 and the pad 23 defines a length 32. The spring member 15 is centrally located along the length 32 of the pad 23. The length 31 of the spring member 15 is between about one-half to three-quarters of the length 32 of the pad 23.

The spring member 15 and the pad 23, respectively, include ends 33 and 34. The ends 33 of the spring member 15 are located inwardly from the ends 34 of the pad member 23.

ADHESIVE & LINER

The adhesive 26 is located between the spring member 15 and the backing of the pad 23 such that the entire engaging surface 18 of the spring member 15 wholly adheres with the pad 23.

A surface perimeter area 30 of the pad 23 is formed between the outer edge 16 of the spring member 15 and the peripheral edge 25 of the pad 23. The surface perimeter area 30 includes the adhesive 26 for adhering to skin of the nose 14.

The surface area 17 of the spring 15 includes an adhesive carrier 20 for adhering to the skin of the nose 14.

The adhesive system is preferably No. 1509, Double Coated Medical Tape on Liner from 3M Company, 3M Center, St. Paul, Minn. This product is a double-coated transparent polyethylene film, coated on both sides with a hypoallergenic, pressure-sensitive, acrylate adhesive, supplied on a paper liner. The double coated tape is wound with the liner on the outside of the roll.

The carrier is transparent 3 mil polyethylene film; the adhesive is hypoallergenic, pressure-sensitive acrylate; and the liner is bleached Kraft-Glassine paper, silicone coated on both sides.

USING THE DILATOR

When the spring member 15 is located over the bridge 19 of the nose 14, the opposite flat surfaces 17 and 18 of the spring member 15 extend over the bridge 19 of the nose 14 and at least partly beyond the bridge 19 on both sides of the bridge 19.

In use on the nose 14, there are only the spring member 15, and the adhesive pad 23. There is the adhesive 26 between the pad 23 and the spring member 15, and selectively, in one form of the invention there is also the adhesive carrier 20 on the surface 17 of the spring member 15.

When the pad member 23 is located on the nose 14 of a wearer, the ends 33 of the spring 15 are urged outwardly as indicated by arrows 35 to separate from the skin covering the nasal passages 11 of the wearer. The pad 23 is lifted in part from the nasal passages 12 in the vicinity of the ends 33 of the spring member 15. When in position on the nose 14, a flat surface 17 of the spring member 15 engages directly on the nose 14 through an adhesive 22.

DILATOR PRIOR TO USAGE

When unattached to the nose 14, the spring member 15 and pad 23 have a natural position contrary to a curvature formed by location of the spring member 15 over the bridge 19 of the nose 14 and adjacent to the nasal passages 12 and 13. The resilient spring member 15 and pad 23 preferably have a position with a curvature contrary to the shape of the curvature formed from one nasal passage 12 over the bridge 19 to the second nasal passage 13. The contrary curvature acts to place an increased amount of spring action on the dilator 10 so that the dilation action on the nasal passages 12 and 13 is enhanced when in use. The increased spring action is caused by the counter stress put into the spring member 15 prior to usage by the position of contrary curvature.

The dilator 10 is located in a package 38 before usage on the nose. The interaction of the walls 141 and 40 of the package 38 on the dilator 10 develops the contrary curvature. The shape of the package 38 is such that there is an effective curvature created by the surfaces 144 engaging the dilators 10 when packed. This curvature is a counter curvature 36 relative to the curvature when in use. The wall 141 is loaded by spring 142 to ensure the counter curvature.

Alternatively or additionally, the pad 23 is stretched prior to adhering to the spring 15. The stretch 39 acts to place the contrary curvature 36 onto the dilator 10 as explained in relation to FIG. 6. As the pad material 23 returns to its unstretched mode after the die-cut 46 it causes the spring 15 which adhered to the pad to be pulled into the counter curvature position.

MANUFACTURING THE DILATOR

The method of manufacturing for the dilator 10 requires the resilient spring member 15 to be die cut and located as an island within the surface area 30 of the pad 23.

The various materials: spring 15, pad 23, and adhesive 20, are provided, respectively, on rolls 41, 42 and 43 of material.

The resilient spring 15 is formed of a ribbon material 44 which is die cut at 45 from ribbon material 44.

The pad 23 is die cut at 46 from a second ribbon 47 of material. The release liner 152 removed from the pad 23 is removed as a ribbon to the waste liner roll 53.

The ribbon of resilient material 44 and pad material 47 are adhesively joined together in a webbing operation. The adhesive material 43 in the form of a ribbon 48 is fed into a position at die 45 on one side of the ribbon material 44 so as to place an adhesive on the ribbon material 44 for the spring. The adhesive system 20 is cut at die 45 to conform with the spring 15.

Adhesive 26 on the one side of the pad ribbon material 47 sticks the spring ribbon material 44 to the pad ribbon material 47 at the die 46.

Figure 6A:
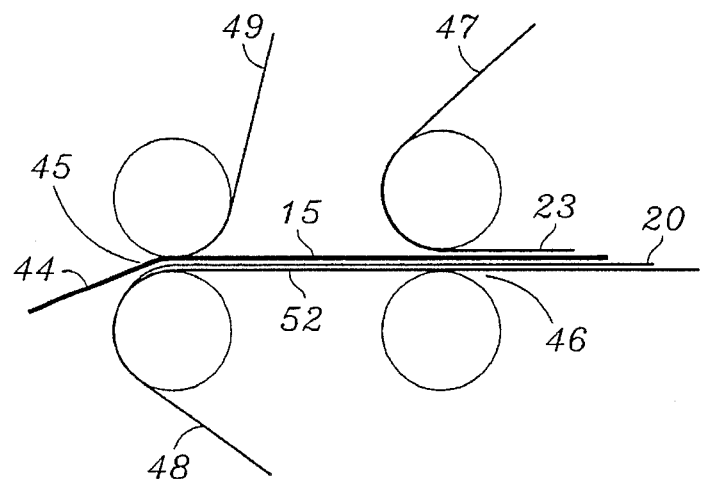
FIG. 6A illustrates side views of the dilator respectively at two different die positions in the construction procedure.

Non-adhering materials, 49, and 51 removed from the respective die cuts 45 and 46 are removed as ribbons of waste material. The material 49 is the unused ribbon material 44, namely the unused resilient material, and unused adhesive 48 which is die-cut 45. The material 51 is the spring 15, the pad 23, and the adhesive 20 which is die-cut 46. FIG. 6A illustrates the sandwiched components of the dilator at the die positions 45 and 46 respectively.

A liner 52 is also provided to cover the adhesive 26 of the pad 23 not covered by the spring 15. The liner is the leftover after the die-cut 45 of the resilient adhesive combination. When in use, the liner 52 is removed to expose the adhesive surface 26 and spring 15. The liner 52 is formed as the paper backing for the two sided adhesive 21 and 22 on carrier 20. The liner 52 is formed as the base of the roll of material 43 for the adhesive ribbon 48.

In some cases, the adhesive ribbon material 48 affixed to the spring ribbon material 44 may be avoided. There may be only the adhesive pad material 47 and the spring ribbon material 44 and a liner provided by a different ribbon material from roll 43. Thus only a paper type liner may be provided from roll 43. In such a situation there is no two sided coated tape.

Multiple dilators 10 are formed in a nested series in the manufacturing process through dies 45 and 46. They are then cut and separated at die 54 prior to packaging.

GENERAL

Many other forms of the invention exist, each differing from others in matters of detail only.

For instance, in some uses of the dilator on the nose, there are may be elements in addition to the basic spring member, the adhesive pad, and the adhesive between the spring and the nose skin. Also, there are situations where the adhesive on the spring for engaging the nose is unnecessary.

In other situations the position of curvature is one which means the pad is non-planar. Thus there could be situations where the curvature is generally along the shape of the nose, but not conforming to the nose. These situations could be, for instance, where a lesser degree of tension is needed to be placed on the nasal passages.

Also, in other cases the dilators may be packaged in a tube.

The invention is to be determined solely in terms of the following claims.

What is claimed is:

1. A nasal dilator for preventing outer wall tissue of nasal passages of a human nose from drawing in during breathing, comprising:

an elongated spring member for bridging a human nose, the spring member having an outer edge and opposite flat surfaces and being for extending over a bridge of the nose and being for engaging the user's nose;

a flexible pad having a surface area and peripheral edge, the pad being for engaging the spring member and extending around the spring member so that there is a surface perimeter area of the pad formed between the outer edge of the spring member and the peripheral edge of the pad, the spring being inset from the peripheral edge of the pad substantially around the pad, and wherein the surface perimeter area includes an adhesive for adhering to skin of the nose; and an adhesive means between the spring member and the pad such that the spring member on one of its flat surfaces adheres with the pad, the arrangement being such that when the spring member is located over the bridge of the nose, the opposite flat surface of the spring member extends over the bridge of the nose and at least partly beyond the bridge on both sides of the bridge, and the surface perimeter area of the pad adheres to the skin of the nose, the arrangement being such that, in use, the spring is located between the nose and the pad.

2. A dilator as claimed in claim 1, wherein the adhesive means for permitting the pad to adhere to the skin of the nose is effected by having the spring member occupy between about 25% to about 50% of the surface area of the pad.

3. A dilator as claimed in claim 1 wherein the adhesive means for permitting the pad to adhere to the skin of the nose is effected by having the spring member be centrally located in the surface area of the pad, and the surface of the spring member be between about one-quarter to about half of the surface area of the pad.

4. A dilator as claimed in claim 1 wherein the adhesive means for permitting the pad to adhere to the skin of the nose is effected by having the spring member define a length and the pad define a length, the spring member being centrally located along the length of the pad, and the length of the spring member be between about one-half to about three-quarters of the length of the pad.

5. A dilator as claimed in claim 1 wherein the adhesive means for permitting the pad to adhere to the skin of the nose is effected by having the pad define a narrow width and a broad width, the narrow width being substantially for location over the bridge of a nose, and the broad width being substantially for location centrally over a nostril portion of the nose, the spring member defining a width, and the width of the spring member being about one-half to about three-quarters of the width of narrow width of the pad.

6. A dilator as claimed in claim 1 wherein the spring member and the pad respectively include ends, the ends of the spring member being located inwardly from the ends of the pad member such that when the pad member is located on the nose of a wearer, the ends of the spring are urged outwardly and separate from skin covering the nasal passages of the wearer, such that the pad is lifted in part from the nasal passages in the vicinity of the ends of the spring member.

7. A dilator as claimed in claim 1 wherein the spring member is formed of a resilient, synthetic resinous material, and the spring member and pad, when unattached to the nose, has a natural position contrary to a curvature formed by location of the spring member over the bridge of the nose and adjacent to the nasal passages, the contrary curvature being non-planar.

8. A dilator as claimed in claim 1 wherein the spring member is a resilient member, the spring member having being die cut and located as an island within the surface area of the pad.

9. A dilator as claimed in claim 1 wherein the pad is an elongated element with rounded ends, such ends being substantially cone-shaped.

10. A dilator as claimed in claim 1 wherein the spring is formed of a material die cut from a first ribbon, and the pad is die cut from a second ribbon, and the ribbons are adhesively joined together in a webbing operation, and wherein non-adhering materials removed from the die cuts are removed as ribbons of waste material.

11. A nasal dilator for preventing outer wall tissue of nasal passages of a human nose from drawing in during breathing, comprising:

an elongated spring member for bridging a human nose, the spring member having an outer edge and opposite flat surfaces and being for extending over a bridge of the nose;

a flexible pad having a surface area and peripheral edge, the pad being for engaging the spring member and extending around the spring member so that there is a surface perimeter area of the pad formed between the outer edge of the spring member and the peripheral edge of the pad, the spring being inset from the peripheral edge of the pad substantially around the pad, and wherein the surface perimeter area includes an adhesive means for adhering to skin of the nose;

an adhesive between the spring member and the pad such that the spring member on one of its flat surfaces adheres with the pad, the arrangement being such that when the spring member is located over the bridge of the nose, the opposite flat surface of the spring member extends over the bridge of the nose and at least partly beyond the bridge on both sides of the bridge, and the surface perimeter area of the pad adheres to the skin of the nose; and wherein, in use on the nose, there are the spring member, the adhesive pad, the adhesive between the pad and the spring member, and means for adhering such spring member directly to the user's nose including an adhesive on the spring member.

12. A dilator as claimed in claim 11 wherein the adhesive means for permitting the pad to adhere to the skin of the nose is effected by having the spring member occupy between about 25% to about 50% of the surface area of the pad.

13. A dilator as claimed in claim 11 wherein the adhesive means for permitting the pad to adhere to the skin of the nose is effected by having the spring member be centrally located in the surface area of the pad, and the surface of the spring member be between about one-quarter to about half of the surface area of the pad.

14. A dilator as claimed in claim 11 wherein the adhesive means for permitting the pad to adhere to the skin of the nose is effected by having the spring member define a length and the pad define a length, the spring member being centrally located along the length of the pad, and the length of the spring member be between about one-half to about three-quarters of the length of the pad.

15. A dilator as claimed in claim 11 wherein the adhesive means for permitting the pad to adhere to the skin of the nose is effected by having the pad define a narrow width and a broad width, the narrow width being substantially for location over the bridge of a nose, and the broad width being substantially for location centrally over a nostril portion of the nose, the spring member defining a width, and the width of the spring member being about one-half to about three-quarters of the width of narrow width of the pad.

16. A dilator as claimed in claim 11 wherein the adhesive means for permitting the pad to adhere to the skin of the nose is effected by having the spring member and the pad respectively include ends, the ends of the spring member being located inwardly from the ends of the pad member such that when the pad member is located on the nose of a wearer, the ends of the spring are urged outwardly and separate from skin covering the nasal passages of the wearer, such that the pad is lifted in part from the nasal passages in the vicinity of the ends of the spring member.

17. A dilator as claimed in claim 11 wherein the spring member is formed of a resilient, synthetic resinous material, and the spring member and pad, when unattached to the nose, has a natural position contrary to a curvature formed by location of the spring member over the bridge of the nose and adjacent to the nasal passages, the contrary curvature being non-planar.

18. A dilator as claimed in claim 11 wherein the spring material and pad have a position, when non-adhering to the nose, with a curvature contrary to the shape of the curvature formed from one nasal passage over the bridge to the second nasal passage.

19. A dilator as claimed in claim 11 wherein the spring member is a resilient material, the spring member having being die cut and located as an island within the surface area of the pad.

20. A dilator as claimed in claim 11 wherein the pad is an elongated element with rounded ends.

21. A dilator as claimed in claim 11 wherein the spring is formed of a material die cut from a first ribbon, and the pad is die cut from a second ribbon, and the ribbons are adhesively joined together in a webbing operation, and wherein non-adhering materials removed from the die cuts are removed as ribbons of waste material.

22. A dilator as claimed in claim 11 including locating the dilator in a package for developing the contrary curvature.

23. A nasal dilator for preventing outer wall tissue of nasal passages of a human nose from drawing in during breathing, comprising:

an elongated spring member for bridging a human nose, the spring member having an outer edge and opposite flat surfaces and being for extending over a bridge of the nose;

a flexible pad having a surface area and peripheral edge, the pad being for engaging the spring member and extending around the spring member so that there is a surface perimeter area of the pad formed between the outer edge of the spring member and the peripheral edge of the pad, the spring being inset from the peripheral edge of the pad substantially around the pad, and wherein the surface perimeter area includes an adhesive for adhering to skin of the nose;

an adhesive between the spring member and the pad such that the spring member on one of its flat surfaces adheres with the pad, the arrangement being such that when the spring member is located over the bridge of the nose, the opposite flat surface of the spring member extends over the bridge of the nose and at least partly beyond the bridge on both sides of the bridge, and the surface perimeter area of the pad adheres to the skin of the nose; and wherein, when in position on the nose, a flat surface of the spring member engages directly on the nose.

24. A dilator as claimed in claim 23 wherein the spring member and pad have a position, when non-adhering to the nose, with a curvature contrary to the shape of the curvature formed from one nasal passage over the bridge to the second nasal passage, such contrary curvature being non-planar.

25. A dilator as claimed in claim 24 including locating the dilator in a package for developing the contrary curvature.

26. A nasal dilator comprising:

an elongated spring member for bridging a human nose, the spring member having an outer edge and opposite flat surfaces and being for extending over a bridge of the nose;

a flexible pad having a surface area, the pad being for engaging the spring member and extending beyond the spring member so that there is a surface area of the pad formed between the outer edge of the spring member and the peripheral edge of the pad, and wherein the surface area includes an adhesive for adhering to skin of the nose;

an adhesive between the spring member and the pad such that the spring member on one of its flat surfaces adheres with the pad, the arrangement being such that when the spring member is located over the bridge of the nose, the spring member extends over the bridge of the nose and at least partly beyond the bridge on both sides of the bridge, and the surface area of the pad adheres to the skin of the nose; and wherein the spring member is formed of a resilient, synthetic resinous material, and the spring member and pad, when unattached to the nose, has a natural position contrary to a curvature formed by location of the spring member over the bridge of the nose and adjacent to the nasal passages, and wherein the position of contrary curvature is obtained by relatively stretching the pad longitudinally prior to affixation with the spring member.

27. A nasal dilator for preventing outer wall tissue of nasal passages of a human nose from drawing in during breathing, comprising:

an elongated spring member for bridging a human nose, the spring member having an outer edge and opposite flat surfaces and being for extending over a bridge of the nose and wherein the spring member is a resilient member;

a flexible pad having a surface area and peripheral edge, the pad being for engaging the spring member and extending around the spring member so that there is a surface perimeter area of the pad formed between the outer edge of the spring member and the peripheral edge of the pad whereby the spring is inset from the peripheral edge of the pad substantially around the pad, and wherein the surface perimeter area includes an adhesive for adhering to skin of the nose; and an adhesive between the spring member and the pad such that the spring member on one of its entire engaging surfaces wholly adheres with the pad, the spring member having being die cut and been located as an island within the surface area of the pad, the arrangement being such that when the spring member is located over the bridge of the nose, the opposite flat surfaces of the spring member extend over the bridge of the nose and at least partly beyond the bridge on both sides of the bridge, and the surface perimeter area of the pad adheres to the skin of the nose, and wherein in use on the nose there are only the spring member with adhesive for adhering to the nose, the adhesive pad, and the adhesive between the pad and the spring member with the spring member being positioned between the nose and the pad.

28. A dilator as claimed in claim 27 wherein the spring member defines a length and the pad defines a length, and wherein the spring member is centrally located along the length of the pad, and the length of the spring member is between about one-half to three-quarters of the length of the pad.

29. A nasal dilator for preventing outer wall tissue of nasal passages of a human nose from drawing in during breathing, comprising:

an elongated spring member for bridging a human nose, the spring member having an outer edge and opposite flat surfaces and being for extending over a bridge of the nose;

a flexible pad having a surface area and peripheral edge, the pad being for engaging the spring member and extending around the spring member so that there is a surface perimeter area of the pad formed between the outer edge of the spring member and the peripheral edge of the pad whereby the spring is inset from the peripheral edge of the pad substantially around the pad, and wherein the surface perimeter area includes an adhesive for adhering to skin of the nose;

the spring member and the pad, respectively, including ends, the ends of the spring member being located inwardly from the ends of the pad member such that when the pad member is located on the nose of a wearer, the ends of the spring are urged outwardly and separate from nostrils of the wearer, such that the pad is lifted in part from the nostrils in the vicinity of the ends of the spring member, and the resilient member and pad have a position, when non-adhering to the nose, with a curvature contrary to the shape of the curvature formed from one nasal passage over the bridge to the second nasal passage with the spring member being positioned between the nose and the pad.

30. A dilator as claimed in claim 29 including locating the dilator in a package for developing the contrary curvature.

31. A system for preventing outer wall tissue of nasal passages of a human nose from drawing in during breathing comprising:

a nasal dilator acting in operative position to adopt a curvature formed by location over a bridge of the nose and adjacent to the nasal passages, and the dilator including an elongated spring member for bridging a human nose, and a flexible pad being for engaging the spring member, the pad including an adhesive for adhering to skin of the nose; and the spring being for engaging the skin of the nose, the arrangement being such that, in use, the spring is located between the nose and the pad.

32. A nasal dilator for preventing outer wall tissue of nasal passages of a human nose from drawing in during breathing, comprising:

an elongated spring member for bridging a human nose, the spring member having an outer edge and opposite flat surfaces and being for extending over a bridge of the nose and wherein the spring member is a resilient member;

a flexible pad having a surface area and peripheral edge, the pad being for engaging the spring member and extending around the spring member so that there is a surface perimeter area of the pad formed between the outer edge of the spring member and the peripheral edge of the pad, the spring being inset from the peripheral edge of the pad substantially around the pad, and wherein the surface perimeter area includes an adhesive for adhering to skin of the nose;

an adhesive between the spring member and the pad such that the spring member on one of its flat surfaces adheres with the pad, the spring member having being die cut and been located as an island within the surface area of the pad, the arrangement being such that when the spring member is located over the bridge of the nose, the opposite flat surface of the spring member extends over the bridge of the nose and at least partly beyond the bridge on both sides of the bridge, and the surface perimeter area of the pad adheres to the skin of the nose, and wherein in use on the nose there are only the spring member with adhesive for adhering to the nose, the adhesive pad, and the adhesive between the pad and the spring member; and wherein, when in position on the nose, a flat surface of the spring member with adhesive engages directly to the user's nose.

33. A dilator as claimed in claim 32 wherein the means for permitting the pad to adhere to the skin of the nose is effected by having the spring member define a length and the pad define a length, the spring member being centrally located along the length of the pad, and the length of the spring member being between about one-half to about three-quarters of the length of the pad.

34. A nasal dilator comprising:

an elongated spring member for bridging a human nose and for engaging a user's nose;

a flexible pad having a surface area, the pad being for engaging the spring member and extending beyond the spring member so that there is a surface area of the pad formed between the outer edge of the spring member and the peripheral edge of the pad, and wherein the surface area includes an adhesive for adhering to skin of the nose; and an adhesive means between the spring member and the pad such that the spring member adheres with the pad, the arrangement being such that when the spring member is located over the bridge of the nose, the spring member extends over the bridge of the nose and at least partly beyond the bridge on both sides of the bridge, and the surface area of the pad adheres to the skin of the nose, the arrangement being such that, in use, the spring is located between the nose and the pad.

35. A dilator as claimed in claim 34 wherein the adhesive means for permitting the pad to adhere to the skin of the nose is effected by having the spring member occupy between about 25% to about 50% of the surface area of the pad.

36. A dilator as claimed in claim 34 wherein the adhesive means for permitting the pad to adhere to the skin of the nose is effected by having the spring member be centrally located in the surface area of the pad, and the surface of the spring member be between about one-quarter to about half of the surface area of the pad.

37. A dilator as claimed in claim 34 wherein the adhesive means for permitting the pad to adhere to the skin of the nose is effected by having the spring member define a length and the pad define a length, and wherein the spring member being centrally located along the length of the pad, and the length of the spring member be between about one-half to about three-quarters of the length of the pad.

38. A dilator as claimed in claim 34 wherein the adhesive means for permitting the pad to adhere to the skin of the nose is effected by having the pad define a narrow width and a broad width, the narrow width being substantially for location over the bridge of a nose, and the broad width being substantially for location centrally over a nostril portion of the nose, the spring member defining a width, and the width of the spring member being about one-half to about three-quarters of the width of narrow width of the pad.

39. A dilator as claimed in claim 34 wherein in use on the nose there are only the spring member, the adhesive pad, the adhesive between the pad and the spring member.

40. A nasal dilator comprising:

an elongated spring member for bridging a human nose;

a flexible pad having a surface area, the pad being for engaging the spring member and extending beyond the spring member so that there is a surface area of the pad formed between the outer edge of the spring member and the peripheral edge of the pad, and wherein the surface area includes an adhesive for adhering to skin of the nose;

an adhesive between the spring member and the pad such that the spring member adheres with the pad, the arrangement being such that when the spring member is located over the bridge of the nose, the spring member extends over the bridge of the nose and at least partly beyond the bridge on both sides of the bridge, and the surface area of the pad adheres to the skin of the nose; and wherein, when in position on the nose, the spring member engages directly on the nose.

41. A dilator as claimed in claim 40 wherein the spring member and the pad respectively include ends, the ends of the spring member being located inwardly from the ends of the pad member such that when the pad member is located on the nose of a wearer, the ends of the spring are urged outwardly and separate from skin covering the nasal passages of the wearer, such that the pad is lifted in part from the nasal passages in the vicinity of the ends of the spring member.

42. A nasal dilator comprising:

only one elongated spring member for bridging a human nose;

a flexible pad having a surface area, the pad being for engaging the spring member and extending beyond the spring member so that there is a surface area of the pad formed between the outer edge of the spring member and the peripheral edge of the pad, and wherein the surface area includes an adhesive for adhering to skin of the nose;

adhesive means with the pad, the adhesive means being between the spring member and the pad such that the spring member adheres with the pad, the arrangement being such that when the spring member is located over the bridge of the nose, the spring member extends over the bridge of the nose and at least partly beyond the bridge on both sides of the bridge; and the spring member being centrally located in the surface area of the pad, and the surface of the spring member being between about one-quarter to about half of the surface area of the pad and being positioned between the nose and the pad.

43. A nasal dilator comprising:

only one elongated spring member for bridging a human nose;

a flexible pad having a surface area, the pad being for engaging the spring member and extending beyond the spring member so that there is a surface area of the pad formed between the outer edge of the spring member and the peripheral edge of the pad, and wherein the surface area includes an adhesive for adhering to skin of the nose;

adhesive means between the spring member and the pad such that the spring member adheres with the pad, the arrangement being such that when the spring member is located over the bridge of the nose, the spring member extends over the bridge of the nose and at least partly beyond the bridge on both sides of the bridge, and the surface area of the pad adheres to the skin of the nose and the spring member is positioned between the nose and the pad; and the spring member defines a length and the pad defines a length, and wherein the spring member is centrally located along the length of the pad, and the length of the spring member is between about one-half to about three-quarters of the length of the pad.

44. A nasal dilator comprising:

an elongated spring member for bridging a human nose;

a flexible pad having a surface area, the pad being for engaging the spring member and extending beyond the spring member so that there is a surface area of the pad formed between the outer edge of the spring member and the peripheral edge of the pad, and wherein the surface area includes an adhesive for adhering to skin of the nose;

an adhesive between the spring member and the pad such that the spring member adheres with the pad, the arrangement being such that when the spring member is located over the bridge of the nose, the spring member extends over the bridge of the nose and at least partly beyond the bridge on both sides of the bridge, and the surface area of the pad adheres to the skin of the nose; and wherein, when in position on the nose, the spring member engages directly on the nose.

* * * * *

UNITED STATES PATENT AND TRADEMARK OFFICE
CERTIFICATE OF CORRECTION

PATENT NO. : 5,546,929

DATED : August 20, 1996

INVENTOR(S) : Jerome D. Muchin

It is certified that error appears in the above-identified patent and that said Letters Patent is hereby corrected as shown below:

In [76] Inventor: delete "Constock" and insert --Comstock--.

In Column 12, Claim 43, line 36, delete "and" after the word "bridge".

Signed and Sealed this

Thirty-first Day of December, 1996

*Attest:*

BRUCE LEHMAN

*Attesting Officer*    Commissioner of Patents and Trademarks